United States Patent
Gao et al.

(10) Patent No.: US 12,168,642 B2
(45) Date of Patent: *Dec. 17, 2024

(54) PROCESS FOR PRODUCING 4,4'-DICHLORODIPHENYL SULFOXIDE

(71) Applicant: BASF SE, Ludwigshafen am Rhein (DE)

(72) Inventors: Jun Gao, Ludwigshafen am Rhein (DE); Indre Thiel, Ludwigshafen am Rhein (DE); Christian Schuetz, Ludwigshafen am Rhein (DE); Lukas Metzger, Ludwigshafen am Rhein (DE); Oliver Bey, Ludwigshafen am Rhein (DE); Stefan Blei, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 495 days.

This patent is subject to a terminal disclaimer.

(21) Appl. No.: 17/429,210

(22) PCT Filed: Feb. 6, 2020

(86) PCT No.: PCT/EP2020/052970
§ 371 (c)(1),
(2) Date: Aug. 6, 2021

(87) PCT Pub. No.: WO2020/161228
PCT Pub. Date: Aug. 13, 2020

(65) Prior Publication Data
US 2022/0098147 A1    Mar. 31, 2022

Related U.S. Application Data

(60) Provisional application No. 62/803,045, filed on Feb. 8, 2019.

(30) Foreign Application Priority Data

Feb. 8, 2019 (EP) .................................... 19156196

(51) Int. Cl.
C07C 315/00 (2006.01)
C07C 315/02 (2006.01)
C07C 315/06 (2006.01)

(52) U.S. Cl.
CPC .......... *C07C 315/00* (2013.01); *C07C 315/02* (2013.01); *C07C 315/06* (2013.01)

(58) Field of Classification Search
CPC .............. C07C 315/00; C07C 315/06
See application file for complete search history.

(56) References Cited

U.S. PATENT DOCUMENTS

| 4,871,876 A | 10/1989 | Schaefer et al. |
| 6,323,341 B1 | 11/2001 | Agterberg et al. |
| 2022/0267261 A1* | 8/2022 | Gao ............... C07C 315/02 |

FOREIGN PATENT DOCUMENTS

| CN | 102351756 A | 2/2012 |
| CN | 102351757 A | 2/2012 |
| CN | 102351758 A | 2/2012 |
| CN | 104402780 A | 3/2015 |
| CN | 104557626 A | 4/2015 |
| CN | 108047101 A | 5/2018 |
| JP | 51-010459 A | 1/1976 |
| JP | 2000-001456 A | 1/2000 |
| JP | 2002-507597 A | 3/2002 |
| JP | 2003-210942 A | 7/2003 |
| SU | 0765262 A1 | 9/1980 |

OTHER PUBLICATIONS

International Search Report and Written Opinion received for PCT Patent Application No. PCT/EP2020/052970, mailed on Apr. 23, 2020, 10 pages.
Sun et al., "Formation of diphenyl sulfoxide and diphenyl sulfide via the aluminum chloride-facilitated electrophilic aromatic substitution of benzene with thionyl chloride, and a novel reduction of sulfur(IV) to sulfur(II)", Phosphorus, Sulfur, and Silicon, vol. 185, 2010, pp. 2535-2542.
Sun et al., "Investigations on the Lewis-acids-catalysed electrophilic aromatic substitution reactions of thionyl chloride and selenyl chloride, the substituent effect, and the reaction mechanisms", Journal of Chemical Research, 2013, pp. 736-744.
Sun et al., "Iron(III) chloride (FeCl 3 )-catalyzed electrophilic aromatic substitution of chlorobenzene with thionyl chloride (SOCl 2 ) and the accompanying auto-redox in sulfur to give diaryl sulfides (Ar 2 S): Comparison to catalysis by aluminum chloride (AlCl 3 )", Phosphorus, Sulfur and Silicon, vol. 192, No. 3, 2017, pp. 376-380.

(Continued)

*Primary Examiner* — Rosalynd A Keys
(74) *Attorney, Agent, or Firm* — Faegre Drinker Biddle & Reath LLP

(57) ABSTRACT

The invention relates to a process for producing 4,4'-dichlorodiphenyl sulfoxide comprising: (I) reacting thionyl chloride, chlorobenzene and aluminum chloride in a molar ratio of thionyl chloride:chlorobenzene:aluminum chloride of 1:(6 to 9):(1 to 1.5) at a temperature in the range from 0 to below 20° C., forming an intermediate reaction product and hydrogen chloride; (II) mixing aqueous hydrochloric acid and the intermediate reaction product at a temperature in the range from 70 to 110° C. to obtain an organic phase comprising 4,4'-dichlorodiphenyl sulfoxide and an aqueous phase; (III) cooling the organic phase comprising the 4,4'-dichlorodiphenyl sulfoxide to a temperature below the saturation point of 4,4'-dichlorodiphenyl sulfoxide to obtain a suspension comprising crystallized 4,4'-dichlorodiphenyl sulfoxide; (IV) solid-liquid-separation of the suspension to obtain a residual moisture containing solid 4,4'-dichlorodiphenyl sulfoxide comprising crystallized 4,4'-dichlorodiphenyl sulfoxide and mother liquor.

13 Claims, 1 Drawing Sheet

(56) References Cited

OTHER PUBLICATIONS

International Preliminary Report on Patentability received for PCT Patent Application No. PCT/EP2020/052970, mailed on Aug. 19, 2021, 8 pages.
Asaoka et al., "Study on Formation of Ice Slurry Using Ethanol Solution with Vacuum Evaporation", vol. 23, Issue 2, pp. 165-174, 2006.
Fieser et al., "p-TOLUYL-o-BENZOIC ACID", Organic Synthesis, vol. 4, No. 73, 1925.

\* cited by examiner

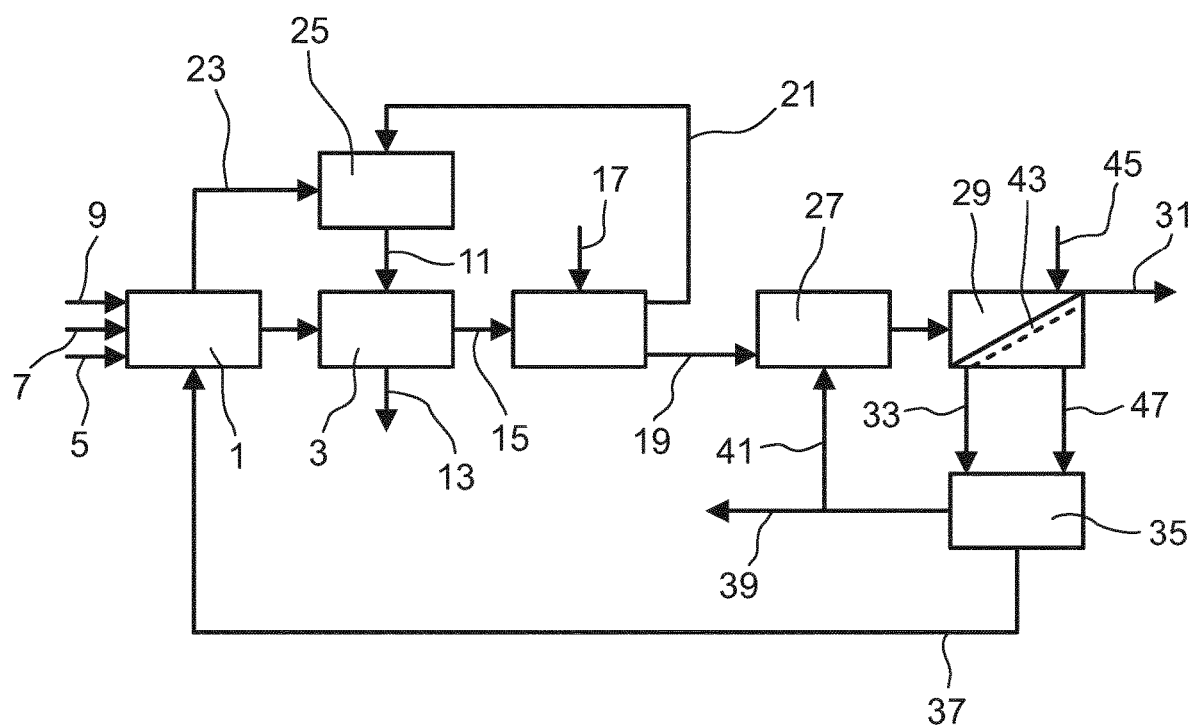

PROCESS FOR PRODUCING 4,4'-DICHLORODIPHENYL SULFOXIDE

CROSS-REFERENCE TO RELATED APPLICATIONS

This application is a national stage application (under 35 U.S.C. § 371) of PCT/EP2020/052970, filed Feb. 6, 2020, which claims benefit of European Application No. 19156196.8, filed Feb. 8, 2019, and U.S. Application No. 62/803,045, filed Feb. 8, 2019, all of which are incorporated herein by reference in their entirety.

The invention relates to a process for producing 4,4'-dichlorodiphenyl sulfoxide which also is called 1-chloro-4 (4-chlorophenyl)sulfinyl benzene or bis(4-chlorophenyl) sulfoxide.

4,4'-dichlorodiphenyl sulfoxide (in the following DCDPSO) can be used as a precursor for producing 4,4-dichlorodiphenyl sulfone which is used for example as a monomer for preparing polymers such as polyarylene ethers like polysulfone, polyether sulfone, or polyphenylene sulfone or as an intermediate of pharmaceuticals, dyes and pesticides.

For the production of DCDPSO several processes are known. One process is a Friedel-Crafts reaction with thionyl chloride and chlorobenzene as starting materials in the presence of a catalyst, for example aluminum chloride. Generally, the reaction of thionyl chloride and chlorobenzene is disclosed as a first part in the production of 4,4'-dichlorodiphenyl sulfone, whereby an intermediate reaction product is obtained by the reaction of thionyl chloride and chlorobenzene which is hydrolyzed at an elevated temperature and thereafter oxidized to yield 4,4'-dichlorodiphenyl sulfone.

General processes for the production of sulfur containing diaryl compounds are disclosed for example in Sun, X. et al, "Investigations on the Lewis-acids-catalysed electrophilic aromatic substitution reactions of thionyl chloride and selenyl chloride, the substituent effect, and the reaction mechanisms", Journal of Chemical Research 2013, pages 736 to 744, Sun, X. et al, "Formation of diphenyl sulfoxide and diphenyl sulfide via the aluminum chloride-facilitated electrophilic aromatic substitution of benzene with thionyl chloride, and a novel reduction of sulfur(IV) to sulfur(I1)", Phosphorus, Sulfur, and Silicon, 2010, Vol. 185, pages 2535-2542 and Sun, X. et al., "Iron(II) chloride ($FeCl_3$)-catalyzed electrophilic aromatic substitution of chlorobenzene with thionyl chloride ($SOCl_2$) and the accompanying auto-redox in sulfur to give diaryl sulfides ($Ar_2S$): Comparison to catalysis by aluminum chloride ($AlCl_3$)", Phosphorus, Sulfur, and Silicon, 2017, Vol. 192, No. 3, pages 376 to 380. In these papers different reaction conditions and catalysts are compared.

Friedel-Crafts acylation reactions of thionyl chloride and chlorobenzene in the presence of Lewis acid catalyst as part in the production of 4.4'-dichlorodiphenylsulfone are also disclosed for instance in CN-A 108047101, CN-A 102351756, CN-A 102351757, CN-A 102351758 or CN-A 104557626.

A two-stage process for producing 4,4'-dichlorodiphenyl sulfone where in the first stage DCDPSO is produced is disclosed in CN-B 104402780. For producing DCDPSO, a Friedel-Crafts reaction is described to be carried out at 20 to 30° C. using thionyl chloride and chlorobenzene as raw material and anhydrous aluminum chloride as catalyst. The Friedel-Crafts reaction is followed by cooling, hydrolysis, heating and refluxing. It is further described that after reflux is finished the reaction mixture is cooled down and DCDPSO precipitates in form of white crystals which are filtered off. The DCDPSO then is oxidized to obtain 4,4'-dichlorodiphenyl sulfone.

SU-A 765262 also discloses a two-stage process for producing 4,4'-dichlorodiphenyl sulfone where in the first stage DCDPSO is obtained by a Friedel-Crafts reaction using thionyl chloride and chlorobenzene in the presence of aluminum chloride at a temperature in the range from −10 to 50° C. According to the examples, the mixture obtained in the Friedel-Crafts reaction is poured into a 3% aqueous solution of hydrochloric acid and heated to completely dissolve the DCDPSO in the chlorobenzene which is added in excess. After separation into two phases, the organic phase is washed and then cooled to precipitate the DCDPSO. In one example the hydrochloric acid is obtained by trapping the hydrogen chloride evolved in the Friedel-Crafts reaction.

It is an object of the present invention to provide a reliable and energy-efficient process for producing DCDPSO with a reduced amount of impurities, particularly with a reduced amount of isomers like 2,4'-dichlorodiphenyl sulfoxide, 3,4'-dichlorodiphenylsulfoxide and 2,2'-dichlorodiphenyl sulfoxide.

This object is achieved by a process for producing DCDPSO comprising:
(I) reacting thionyl chloride, chlorobenzene and aluminum chloride in a molar ratio of thionyl chloride:chlorobenzene:aluminum chloride of 1:(6 to 9):(1 to 1.5) at a temperature in the range from 0 to below 20° C., forming an intermediate reaction product and hydrogen chloride;
(II) mixing aqueous hydrochloric acid and the intermediate reaction product at a temperature in the range from 70 to 110° C. to obtain an organic phase comprising DCDPSO and an aqueous phase;
(III) cooling the organic phase comprising the DCDPSO to a temperature below the saturation point of DCDPSO to obtain a suspension comprising crystallized DCDPSO;
(IV) solid-liquid-separation of the suspension to obtain a residual moisture containing solid DCDPSO, wherein the residual moisture containing solid DCDPSO comprises crystallized DCDPSO and mother liquor.

By this process 4,4'-dichlorodiphenyl sulfoxide is obtained which contains less than 0.5 wt % isomers based on the total amount of all isomers of dichlorodiphenyl sulfoxide.

It is a further advantage of this process that the reaction product comprising DCDPSO is essentially free of aluminum chloride used as catalyst. "Essentially free" in this context means that, if at all detectable, there are only traces of aluminum chloride in the product obtained from the process, preferably, the amount of aluminum chloride is from 0 to 100 ppm, particularly less than 50 ppm.

To obtain DCDPSO, in the reaction (I) thionyl chloride, chlorobenzene and aluminum chloride are fed into a reactor in a molar ratio of thionyl chloride:chlorobenzene:aluminum chloride of 1:(6 to 9):(1 to 1.5), preferably in a molar ratio of thionyl chloride:chlorobenzene:aluminum chloride of 1:(6 to 8):(1 to 1.2) and particularly in a molar ratio of thionyl chloride:chlorobenzene:aluminum chloride of 1:(6 to 7):(1 to 1.1).

The reactor can be any reactor which allows mixing and reacting of the components fed into the reactor. A suitable reactor is for example a stirred tank reactor or jet loop reactor. If a stirred tank reactor is used, the stirrer preferably is an axially conveying stirrer, for example an oblique blade agitator. The reaction can be operated either continuously or batchwise. Preferably, the reaction is operated batchwise.

The thionyl chloride, chlorobenzene and aluminum chloride can be added simultaneously or successively. For reasons of ease of conduct of the reaction—in particular in case of batch reaction—preferably, aluminum chloride and chlorobenzene are fed firstly into the reactor and then the thionyl chloride is added to the aluminum chloride and chlorobenzene. In this case the aluminum chloride and chlorobenzene can be added simultaneously or one after the other. However, in each case it is preferred to mix the aluminum chloride and chlorobenzene before adding the thionyl chloride. Particularly preferably aluminum chloride and chlorobenzene are first fed into the reactor and the thionyl chloride is added to the aluminum chloride and chlorobenzene. During the reaction hydrogen chloride (HCl)—typically in gaseous form—is formed which is at least partially withdrawn from the reactor. The volumetric flow for adding the thionyl chloride typically depends on heat dissipation and flow rate of the gas withdrawn from the reactor.

The chlorobenzene which is added in excess into the reactor and, therefore, only partially converted during the chemical reaction, also serves as a solvent for the reaction products. In any step of the process in which a solvent is used, the solvent preferably is chlorobenzene. Due to the reaction conditions in the context of the present invention, the person skilled in the art appreciates that the term "chlorobenzene" means monochlorobenzene which may contain traces of impurities.

The thionyl chloride and the chlorobenzene react in the presence of the aluminum chloride whereby an intermediate reaction product and hydrogen chloride form. The intermediate reaction product comprises 4,4'-dichlorodiphenyl sulfoxide-AlCl$_3$ adduct. The aluminum chloride generally can act as catalyst. The chemical reaction can be schematically represented by the following chemical reaction equation (1):

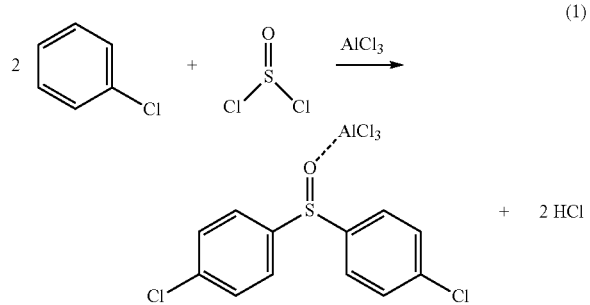

The reaction (I) is carried out at a temperature in the range from 0 to below 20° C., preferably at a temperature in the range from 3 to 15° C. and particularly in the range from 5 to 12° C.

Thereby the reaction can be carried out at a constant or almost constant temperature. It is also possible to carry out the reaction at varying temperatures within the described ranges, for instance employing a temperature profile over the time of reaction or the reactor.

The reaction period generally depends on the amounts of reactants used and increases with increasing amounts of reactants. After addition of the thionyl chloride to the mixture of aluminum chloride and chlorobenzene is completed, the reaction preferably is continued for 10 to 120 min, more preferred from 20 to 50 min after the total amount of thionyl chloride is fed into the reactor.

Independently of whether the reaction is operated continuously or batchwise, the flow rate of the thionyl chloride is selected such that the heat generated by the reaction can be dissipated from the reactor by suitable cooling devices to keep the temperature in the reactor within a predefined range.

The hydrogen chloride (HCl) produced in the reaction typically is in gaseous form and at least partly removed from the reactor. While it can be put to other use in gaseous form, preferably, the hydrogen chloride removed from the reaction is mixed with water to produce aqueous hydrochloric acid.

After the reaction the intermediate reaction product is mixed with aqueous hydrochloric acid. For reasons of energy as well as production efficiency as well as sustainability, particularly preferably, the aqueous hydrochloric acid is produced from the hydrogen chloride removed from the reaction (I). By mixing the intermediate reaction product with the aqueous hydrochloric acid hydrolysis of the intermediate reaction product can take place. A crude reaction product comprising DCDPSO is obtained. The crude reaction product can also comprise aluminum chloride which is typically in hydrated form, usually as AlCl$_3$·6H$_2$O. The hydrolysis can be schematically represented by reaction equation (2):

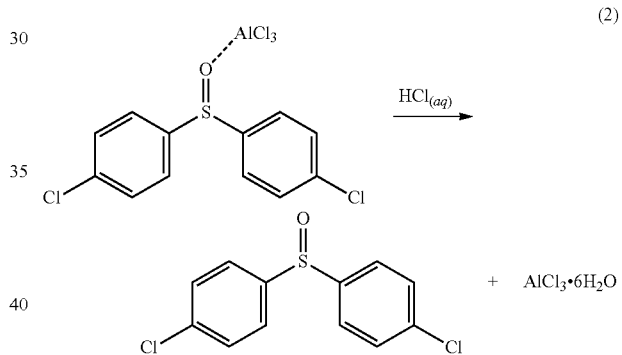

The temperature at which the hydrolysis is carried out is in the range from 70 to 110° C., preferably in the range from 80 to 100° C. and particularly in the range from 80 to 90° C. The reaction period of the hydrolysis after all components for the hydrolysis are added preferably is in the range from 30 to 120 min, more preferred in the range from 30 to 60 min and particularly in the range from 30 to 45 min. This reaction period is sufficient for hydrolysis of the intermediate reaction product to obtain the DCDPSO. To facilitate the hydrolysis and to bring it as fast as possible to completion, the mixture can be agitated, preferably the mixture is stirred. After finishing the hydrolysis, the mixture separates into an aqueous phase comprising the AlCl$_3$ and an organic phase comprising DCDPSO solved in the excess chlorobenzene. In case the mixture is stirred, stirring is stopped to allow the mixture to separate.

The aqueous hydrochloric acid may have any concentration. However, a concentration of the hydrochloric acid above 3 wt % improves the solubility of the aluminum chloride. Preferably, the aqueous hydrochloric acid used in the hydrolysis has a concentration in the range from 3 to 12 wt %, more preferably in the range from 6 to 12 wt % and particularly preferably in the range from 10 to 12 wt %. All concentrations of hydrochloric acid in wt % above and in the following are based on the total amount of hydrogen chloride and water in the aqueous hydrochloric acid. An advantage of a higher concentration, particularly of a concentration in the range from 10 to 12 wt % is that the density of the aqueous phase increases and the aqueous phase thus forms the lower phase whereas the upper phase is the organic phase comprising the DCDPSO, in the following also termed as "organic phase". This allows an easier draining of the aqueous phase to obtain the organic phase. Further, the higher concentration allows a smaller amount of water for removing the aluminum chloride. A higher concentration of the aqueous hydrochloric acid further results in a quicker phase separation.

The amount of aqueous hydrochloric acid used in (II) preferably is such that no aluminum chloride precipitates and that further two liquid phases are formed, the lower phase being the aqueous phase and the organic phase being the upper phase. To achieve this, the amount of aqueous hydrochloric acid added to the reaction mixture preferably is such that after the hydrolysis the weight ratio of aqueous to organic phase is in the range from 0.6 to 1.5 kg/kg, more preferably in the range from 0.7 to 1.0 kg/kg and particularly in the range from 0.8 to 1.0 kg/kg. A smaller amount of aqueous hydrochloric acid may result in precipitation of aluminum chloride. Particularly at higher concentrations of the aqueous hydrochloric acid a larger amount is necessary to avoid precipitation. Therefore, the concentration of the aqueous hydrochloric acid preferably is kept below 12 wt %.

The reaction of thionyl chloride, chlorobenzene and aluminum chloride and the mixing with aqueous hydrochloric acid and thus the hydrolysis can be carried out in the same reactor or in different reactors. Preferably, the reaction is carried out in a first reactor and the hydrolysis in a second reactor. If a first reactor and a second reactor are used, the first reactor corresponds to the reactor as described above. The second reactor also can be any reactor to perform a batchwise reaction and which allows stirring of the components in the reactor. Therefore, the second reactor also preferably is a stirred tank reactor.

Either the one reactor, if the reaction and the hydrolysis are carried out in the same reactor, is or the preferably used first and second reactors are designed in such a way that the temperature can be set to adjust the temperature in the reactor. For this purpose it is for example possible to provide a pipe inside the reactor through which a heating medium or a cooling medium can flow. Under the aspect of ease of reactor maintenance and/or uniformity of heating, preferably, the reactor comprises a double jacket through which the heating medium or cooling medium can flow. Besides the pipe inside the reactor or the double jacket the heating and/or cooling of the reactor(s) can be performed in each manner known to a skilled person.

If the reaction and the hydrolysis are carried out in different reactors, it is particularly preferred to heat the intermediate reaction product to a temperature which is above the solubility point of the intermediate reaction product in the solvent after the reaction is completed and prior to transporting the intermediate reaction product from the first reactor to the second reactor. Due to heating the intermediate reaction product before transporting and feeding into the second reactor, the intermediate reaction product dissolves and a liquid without solid components is transported. This has the advantage that fouling of the first reactor is avoided.

The solubility point denotes the temperature of the reaction mixture at which the intermediate reaction product is fully dissolved in the solvent. This temperature depends on the concentration of the intermediate reaction product in the solvent. The lower the concentration of DCDPSO in the organic phase, the lower the temperature is at which the intermediate reaction product is fully dissolved in the solvent.

If the reaction and the hydrolysis are carried out in the same reactor, the aqueous hydrochloric acid is fed into the reactor after the reaction is completed and after the intermediate reaction product is heated to the temperature of the hydrolysis. The flow rate of the aqueous hydrochloric acid preferably is set such that the temperature of the hydrolysis can be held in the specified range for the hydrolysis by tempering the reactor. If the reaction and the hydrolysis are carried out in different reactors, it is preferred to firstly feed the aqueous hydrochloric acid into the second reactor and to add the intermediate reaction product to the aqueous hydrochloric acid. In this case the flow rate of adding the intermediate reaction product into the second reactor is set such that the temperature in the second reactor is held within the specified temperature limits for the hydrolysis by tempering the second reactor.

To remove the aqueous hydrochloric acid and remainders of the aluminum chloride from the organic phase, the organic phase obtained in (II) preferably is separated off and washed with an extraction liquid before cooling in (III).

The phase separation following the hydrolysis can be carried out in the reactor in which the hydrolysis took place or in a separate vessel for phase separation. Under the aspect of less complexity, preferably the phase separation is carried out in the reactor in which the hydrolysis took place. After the phase separation is completed, the aqueous phase and the organic phase are removed separately from the vessel in which the phase separation took place, preferably the reactor in which the hydrolysis was performed. Using aqueous hydrochloric acid having a higher concentration for removing aluminum chloride, particularly aqueous hydrochloric acid having a concentration in the range from 10 to 12 wt % so that the density of the aqueous phase increases and the aqueous phase thus forms the lower phase, has the additional advantage that for the easier draining of the aqueous phase the washing of the organic phase can be carried out in the same apparatus as the hydrolysis.

After being separated off, the organic phase is washed to remove residual aluminum chloride and hydrochloric acid. The extraction liquid used for washing the organic phase preferably is water. Particularly preferably, the water which is used for washing the organic phase is separated off after washing and mixed with the hydrogen chloride obtained in (I) to obtain the aqueous hydrochloric acid.

The washing preferably is carried out in a separate washing vessel. However, it is also possible to only remove the aqueous phase from the reactor in which the hydrolysis took place and carry out the washing step in the reactor in which the hydrolysis took place. If the washing is carried out in a separate washing vessel, any vessel in which an organic phase can be washed can be used. The washing vessel usually comprises means to intimately mix the organic phase with the extraction liquid. Preferably, the washing vessel is a stirred tank into which the organic phase and the extraction liquid are fed and then mixed.

If the phase separation is carried out in a vessel for phase separation, the washing either can be carried out in a washing vessel or, alternatively, in the vessel for phase separation. If phase separation and washing are carried out in the same vessel, it is necessary to provide means for mixing the organic phase with the extraction liquid after the aqueous phase which was separated from the organic phase is drained off.

The washing preferably is carried out at a temperature in the range from 70 to 110° C., more preferred in a range from 80 to 100° C. and particularly in a range from 80 to 90° C. Particularly preferably the washing is carried out at the same temperature as the hydrolysis.

Generally, the amount of extraction liquid which preferably is water is sufficient to remove all or essentially all of the aluminum chloride from the organic phase. Under the aspect of waste control it is usually preferred to use as little extraction liquid as possible. The amount of water used for washing preferably is chosen in such a way that a weight ratio of aqueous to organic phase in the range from 0.3 to 1.2 kg/kg, more preferably in the range from 0.4 to 0.9 kg/kg and particularly in the range from 0.5 to 0.8 kg/kg is obtained. In terms of sustainability and avoidance of large waste water streams it is preferred to use as little water for the washing step as possible. It is particularly preferred to use such an amount of water that the entire aqueous phase from the washing step can be used to generate the aqueous hydrochloric acid in the concentration needed for hydrolysis. For this purpose, the water which is used for washing is separated off and mixed with the hydrogen chloride obtained in the reaction to obtain the aqueous hydrochloric acid. The mixing of the hydrogen chloride and the water can be performed for example in a washing column into which the gaseous hydrogen chloride and the water are fed. If such a washing column is used, preferably the hydrogen chloride and the water are fed in countercurrent. Besides a washing column all further vessels which allow absorbing the hydrogen chloride in water can be used. Thus, it is possible for example to feed the water into a vessel and to introduce the hydrogen chloride into the water. To introduce the hydrogen chloride into the water, for example a pipe can be used which immerges into the water. For distributing the hydrogen chloride in the water, it is possible to provide the end of the pipe immerging into the water with an immersion head having small holes through which the hydrogen chloride flows into the water. As an alternative, also a frit can be used for distributing the hydrogen chloride in the water.

After a predetermined washing period, mixing is stopped to allow the mixture to separate into an aqueous phase and an organic phase. The aqueous phase and the organic phase are removed from the washing vessel separately. The organic phase comprises the DCDPSO solved in the excess chlorobenzene as solvent. The predetermined washing period preferably is as short as possible to allow for short overall process times. At the same time it needs a sufficient time to allow for the removal of aluminum chloride.

The process may comprise one or more than one such washing cycles. Usually one washing cycle is sufficient.

For separating the DCDPSO from the organic phase, the organic phase is cooled to a temperature below the saturation point of DCDPSO in (III) to obtain a suspension comprising crystallized DCDPSO (in the following also termed as "suspension").

The saturation point denotes the temperature of the organic phase at which DCDPSO starts to crystallize. This temperature depends on the concentration of the DCDPSO in the organic phase. The lower the concentration of DCDPSO in the organic phase, the lower is the temperature at which crystallization starts.

The cooling (III) for crystallizing DCDPSO can be carried out in any crystallization apparatus or any other apparatus which allows cooling of the organic phase, for example an apparatus with surfaces that can be cooled such as a vessel or a tank with cooling jacket, cooling coils or cooled baffles like so called "power baffles".

Cooling of the organic phase for crystallization of the DCDPSO can be performed either continuously or batchwise. To avoid precipitation and fouling on cooled surfaces, it is preferred to carry out the cooling in a gastight closed vessel by
(i) reducing the pressure in the gastight closed vessel;
(ii) evaporating solvent;
(iii) condensing the evaporated solvent by cooling;
(iv) returning the condensed solvent into the gastight closed vessel.

This process allows for cooling the organic phase without cooled surfaces onto which crystallized DCDPSO accumulates and forms a solid layer. This enhances the efficiency of the cooling process. Also, additional efforts to remove this solid layer can be avoided. Therefore, it is particularly preferred to use a gastight closed vessel without cooled surfaces.

To avoid precipitation of the crystallized DCDPSO it is further preferred to agitate the organic phase in the crystallization apparatus. Therefore, a suitable apparatus is for example a stirred tank or a draft-tube crystallizer. If the crystallization apparatus is a stirred tank, any stirrer can be used. The specific power input into the crystallizer by the stirring device preferably is in the range from 0.2 to 0.5 W/kg, more preferred in the range from 0.2 to 0.35 W/kg. Preferably, a stirrer type is used which leads to a rather homogeneous power input without high gradients concerning local energy dissipation.

To crystallize DCDPSO, it is necessary to provide crystal nuclei. To provide the crystal nuclei it is possible to use dried crystals which are added to the organic phase or to add a suspension comprising particulate DCDPSO as crystal nuclei. If dried crystals are used but the crystals are too big, it is possible to grind the crystals into smaller particles which can be used as crystal nuclei. Further, it is also possible to provide the necessary crystal nuclei by applying ultrasound to the organic phase. Preferably, the crystal nuclei are generated in situ in an initializing step.

The initializing step preferably comprises following steps before setting the reduced pressure in step (i):
reducing the pressure in the gastight closed vessel such that the boiling point of the organic phase is in the range from 80 to 95° C.;
evaporating solvent until an initial formation of solids takes place;
increasing the pressure in the vessel and heating the organic phase in the vessel to a temperature in the range from 85 to 100° C.

By reducing the pressure in the vessel such that the boiling point of the organic phase is in the range from 80 to 95° C., more preferred in the range from 83 to 92° C., the following evaporation of solvent leads to a saturated solution and the precipitation of DCDPSO. By the following pressure increase and heating the organic phase in the gastight closed vessel to a temperature in the range from 85 to 100° C., the solidified DCDPSO starts to partially dissolve again. This has the effect that the number of crystal nuclei is reduced which allows producing a smaller amount of crystals with a bigger size. Cooling, particularly by reducing the pressure, can be started immediately after a pre-set temperature within the above ranges is reached to avoid complete dissolving of the produced crystal nuclei. However, it is also possible to start cooling after a dwell time for example of 0.5 to 1.5 h at the pre-set temperature.

For generating the crystal nuclei in the initializing step, it is possible to only evaporate solvent until an initial formation of solids take place. It is also possible to entirely condense the evaporated solvent by cooling and to return all the condensed solvent into the gastight closed vessel. The latter has the effect that the liquid in the gastight closed vessel is cooled and solid forms. A mixture of both approaches, where only a part of the evaporated and condensed solvent is returned into the gas tight vessel, is also viable.

If the cooling and thus the crystallization of DCDPSO is performed batchwise, it is preferred to carry out steps (ii) to (iv) during the pressure reduction in step (i). Thereby, it is particularly preferred to continuously reduce the pressure in step (i) until the temperature in the gastight closed vessel reaches a predefined value in the range from 0 to 45° C., preferably in the range from 10 to 35° C. and particularly in the range from 20 to 30° C. At these predefined temperatures the pressure in the gastight closed vessel typically is in the range from 20 to 350 mbar(abs), more preferred in the range from 20 to 200 mbar(abs) and particularly in the range from 20 to 100 mbar(abs). After the predefined temperature value is reached, pressure reduction is stopped and then the gastight closed vessel is vented until ambient pressure is reached. The temperature profile in the gastight closed vessel preferably is selected such that the organic phase is subjected to a constant supersaturation. These conditions can be achieved by adapting the cooling profile while keeping the temperature below the saturation temperature at the respective concentration of DCDPSO in the liquid phase. In detail the adapted cooling profile is chosen, based on phase equilibria, mass of crystal nuclei, and initial size of the crystal nuclei. Further, to adapt the cooling profile, constant grow rates are assumed. To determine the data for adapting the cooling profile, for example turbidity probes, refractive index probes or ATR-FTIR-probes can be used. The temperature profile and/or pressure profile for example can be stepwise, linear or progressive.

To reduce the solubility of the DCDPSO and thus increase the yield of solidified DCDPSO it is necessary to shift the saturation point. This is possible by continuously reducing the amount of solvent at a constant temperature, for example by evaporating solvent, or by cooling the organic phase at constant concentration. Since reduction of the amount of solvent results in a very viscous suspension when a certain critical concentration is reached, it is preferred to increase the yield of solidified DCDPSO partly by reducing the amount of solvent by evaporation followed by reducing the temperature. For reducing the solubility of DCDPSO in the organic phase and to improve the crystallization, it is possible to additionally add at least one drowning-out agent, for example at least one protic solvent like water, an alcohol, and/or an acid, particularly a carboxylic acid, or at least one highly unpolar solvent like a linear and/or cyclic alkane. With respect to ease of workup water, methanol, ethanol, acetic acid and/or formic acid, particularly water and/or methanol are preferred drowning-out agents.

After reaching ambient pressure the suspension which formed in the gastight closed vessel by the cooling is withdrawn and fed into the solid-liquid-separation (IV).

If the cooling and thus the crystallization of DCDPSO is performed continuously, it is preferred to operate the cooling and crystallization stepwise in at least two steps, particularly in two to three steps. If the cooling and crystallization is carried out in two steps, in a first step the organic phase preferably is cooled to a temperature in the range from 40 to 90° C. and in a second step preferably to a temperature in the range from −10 to 50° C. If the cooling is operated in more than two steps, the first step preferably is operated at a temperature in the range from 40 to 90° C. and the last step at a temperature in the range from −10 to 30° C. The additional steps are operated at temperatures between these ranges with decreasing temperature from step to step. If the cooling and crystallization is performed in three steps, the second step for example is operated at a temperature in the range from 10 to 50° C.

As in the batchwise process, the temperature in the continuously operated process can be set by using apparatus for cooling and crystallization having surfaces to be cooled, for example a cooled jacket, cooling coils or cooled baffles like so called "power baffles". To establish the at least two steps for cooling and crystallization, for each step at least one apparatus for cooling and crystallization is used. To avoid precipitation of DCDPSO, also in the continuous process it is preferred to reduce the temperature by reducing the pressure in the apparatus for cooling and crystallization wherein the apparatus for cooling and crystallization preferably are gastight closed vessels. Suitable apparatus for cooling and crystallization for example are agitated-tank crystallizers, draft-tube crystallizers, horizontal crystallizers, forced-circulation crystallizers or Oslo-crystallizers. The pressure which is set to achieve the required temperature corresponds to the vapor pressure of the organic phase. Due to the pressure reduction, low boilers, particularly solvent, evaporate. The evaporated low boilers are cooled to condense, and the condensed low boilers are returned into the respective apparatus for cooling and crystallization by which the temperature is set.

If the cooling and crystallization is carried out continuously, a stream of the suspension is continuously withdrawn from the apparatus for cooling and crystallization. The suspension then is fed into the solid-liquid-separation (IV). To keep the liquid level in the apparatus for cooling and crystallization within predefined limits, fresh organic phase can be fed into the apparatus in an amount corresponding or essentially corresponding to the amount of suspension withdrawn from the apparatus. The fresh organic phase either can be added continuously or batchwise each time a minimum liquid level in the apparatus for cooling and crystallization is reached. Generally, the process can comprise that hydrolysis (II) is carried out batchwise or continuously and that cooling is carried out batchwise or continuously. Thus, it can comprise that hydrolysis (II) is carried out batchwise and cooling continuously or vice versa. If the hydrolysis in (II) is carried out batchwise and the organic phase shall be added continuously into the apparatus for cooling and crystallization or must be added at times when the hydrolysis is not yet finished or if the hydrolysis is operated continuously and the cooling batchwise, preferably at least one buffer container is used into which the organic phase is fed after being withdrawn from the hydrolysis. From this buffer container the organic phase then is fed into the apparatus for cooling and crystallization.

Independently of being carried out batchwise or continuously, crystallization preferably is continued until the solids content in the suspension in the last step of the crystallization is in the range from 5 to 50 wt %, more preferred in the range from 5 to 40 wt % and particularly in the range from 20 to 40 wt %, based on the mass of the suspension.

Even though the cooling and crystallization can be carried out continuously or batchwise, it is preferred to carry out the cooling and crystallization batchwise and particularly to cool the organic phase by reducing the pressure according to the above described process comprising steps (i) to (iv) to avoid precipitation of crystallized DCDPSO on cooled surfaces of an apparatus for cooling and crystallization. Batchwise cooling and crystallization allows a higher flexibility in terms of operating window and crystallization conditions and is more robust against variations in process conditions.

Independently of whether the cooling and crystallization is performed continuously or batchwise, the solid-liquid-separation (IV) can be carried out either continuously or batchwise, preferably continuously.

If the cooling and crystallization is carried out batchwise and the solid-liquid-separation is carried out continuously, at least one buffer container is used into which the suspension withdrawn from the apparatus used for cooling and crystallization is filled. For providing the suspension a continuous stream is withdrawn from the at least one buffer container and fed into a solid-liquid-separation apparatus. The volume of the at least one buffer container preferably is such that each buffer container is not totally emptied between two filling cycles in which the contents of the apparatus for cooling and crystallization is fed into the buffer container. If more than one buffer container is used, it is possible to fill one buffer container while the contents of another buffer container are withdrawn and fed into the solid-liquid-separation. In this case the at least two buffer containers are connected in parallel. The parallel connection of buffer containers further allows filling the suspension into a further buffer container after one buffer container is filled. An advantage of using at least two buffer containers is that the buffer containers may have a smaller volume than only one buffer container. This smaller volume allows a more efficient mixing of the suspension to avoid sedimentation of the crystallized DCDPSO. To keep the suspension stable and to avoid sedimentation of solid DCDPSO in the buffer container, it is possible to provide the buffer container with a device for agitating the suspension, for example a stirrer, and to agitate the suspension in the buffer container. Agitating preferably is operated such that the energy input by stirring is kept on a minimal level, which is high enough to suspend the crystals but prevents them from breakage. For this purpose, the energy input preferably is in the range from 0.2 to 0.5 W/kg, particularly in the range from 0.25 to 0.4 W/kg.

If the cooling and crystallization and the solid-liquid-separation are carried out batchwise, the contents of the vessel for cooling and crystallization directly can be fed into a solid-liquid-separation apparatus as long as the solid-liquid separation apparatus is large enough to take up the whole contents of the vessel for cooling and crystallization. In this case it is possible to omit the buffer container. It is also possible to omit the buffer container when cooling and crystallization and the solid-liquid-separation are carried out continuously. In this case also the suspension directly is fed into the solid-liquid-separation apparatus. If the solid-liquid separation apparatus is too small to take up the whole contents of the vessel for cooling and crystallization, also for batchwise operation at least one additional buffer container is necessary to allow to empty the crystallization apparatus and to start a new batch.

If the cooling and crystallization are carried out continuously and the solid-liquid-separation is carried out batchwise, the suspension withdrawn from the cooling and crystallization apparatus is fed into the buffer container and each batch for the solid-liquid-separation is withdrawn from the buffer container and fed into the solid-liquid-separation apparatus.

The solid-liquid-separation for example comprises a filtration, centrifugation or sedimentation. Preferably, the solid-liquid-separation is a filtration. In the solid-liquid-separation liquid mother liquor is removed from the solid DCDPSO and residual moisture containing DCDPSO (in the following also termed as "moist DCDPSO") is obtained. If the solid-liquid-separation is a filtration, the moist DCDPSO is called "filter cake".

Independently of whether it is carried out continuously or batchwise, the solid-liquid-separation preferably is performed at ambient temperature or temperatures below ambient temperature, preferably at ambient temperature. It is possible to feed the suspension into the solid-liquid-separation apparatus with elevated pressure for example by using a pump or by using an inert gas having a higher pressure, for example nitrogen. If the solid-liquid-separation is a filtration and the suspension is fed into the filtration apparatus with elevated pressure, the differential pressure necessary for the filtration process is realized by setting ambient pressure to the filtrate side in the filtration apparatus. If the suspension is fed into the filtration apparatus at ambient pressure, a reduced pressure is set to the filtrate side of the filtration apparatus to achieve the necessary differential pressure. Further, it is also possible to set a pressure above ambient pressure on the feed side of the filtration apparatus and a pressure below ambient pressure on the filtrate side or a pressure below ambient pressure on both sides of the filter in the filtration apparatus, wherein also in this case the pressure on the filtrate side must be lower than on the feed side. Preferably, the pressure difference between feed side and filtrate side and thus the differential pressure in the filtration apparatus is in the range from 100 to 6000 mbar (abs), more preferred in the range from 300 to 2000 mbar (abs) and particularly in the range from 400 to 1500 mbar (abs), wherein the differential pressure also depends on the filters used in the solid-liquid-separation (IV).

To carry out the solid-liquid-separation (IV) any solid-liquid-separation apparatus known by the skilled person can be used. Suitable solid-liquid-separation apparatus are for example an agitated pressure nutsche, a rotary pressure filter, a drum filter, a belt filter or a centrifuge. The pore size of the filters used in the solid-liquid-separation apparatus preferably is in the range from 1 to 1000 µm, more preferred in the range from 10 to 500 µm and particularly in the range from 20 to 200 µm.

Particularly preferably, cooling and crystallization is carried out batchwise and the solid-liquid-separation is operated continuously.

As by cooling the majority of DCDPSO crystallizes but still a considerable amount of the DCDPSO remains dissolved in the solvent, the mother liquor withdrawn from the solid-liquid-separation apparatus preferably is concentrated and at least a part of the concentrated mother liquor is recycled into the cooling step (III). Concentration of the mother liquor preferably is performed by distillation or evaporation, preferably by evaporation. By concentrating the mother liquor and recycling the mother liquor into the cooling step (III) it is possible to reduce product loss to a minimum.

The distillation or evaporation for concentrating the mother liquor can be carried out either at ambient pressure or at the reduced pressure, preferably at a pressure in the range from 20 to 800 mbar(abs), more preferred in a range from 50 to 500 mbar(abs), and particularly in a range from 100 to 350 mbar(abs).

During the evaporation process low boilers, particularly solvent, evaporate and are withdrawn. DCDPSO which is a high boiler remains in the liquid mother liquor and thus the concentration of DCDPSO increases. The amount to which the mother liquor is reduced in the evaporation depends on the amount of DCDPSO in the mother liquor and the desired concentration in the concentrated mother liquor. The minimum amount to which the mother liquor can be reduced should be larger than the amount of DCDPSO in the mother liquor. Further, the minimum amount of low boiler which is evaporated should be such that the concentration of DCDPSO in the concentrated mother liquor rises. Thus, depending on the concentration of DCDPSO in the mother liquor, the evaporation process preferably is continued until the amount of mother liquor is reduced to 4 to 80 wt %, more preferred to 4 to 40 wt % and particularly to 4 to 20 wt % of the amount of mother liquor fed into the evaporation apparatus. Suitable evaporation apparatus for example are vessels, preferably stirred vessels, rotary evaporators, thin film evaporators and falling film evaporators. Particularly preferred the evaporation apparatus is a falling film evaporator.

Besides an evaporation process it is also possible to carry out a distillation process for concentrating the mother liquor. In a distillation process the low boilers comprising solvent are removed as a top stream. The concentrated mother liquor usually is withdrawn from the distillation process as a bottom stream. The distillation process for example is carried out in a distillation column. Suitable distillation columns for example are plate columns or packed columns. If packed columns are used, either packed beds or structured packings can be used. A suitable pressure for operating such a distillation column is for instance in the range from 20 mbar(abs) to 800 mbar(abs), preferably 50 to 500 mbar(abs), in particular 100 to 350 mbar(abs). The bottom temperature and the head temperature of the distillation column depend on the pressure and the bottom temperature preferably is in a range from 40 to 110° C., more preferred in a range from 55° C. to 100° C. and particularly in a range from 55 to 80° C. and the head temperature preferably is in a range from 30 to 100° C., more preferred in a range from 45 to 90° C. and particularly in a range from 45 to 80° C.

Evaporation or distillation preferably is continued until the concentration of DCDPSO in the mother liquor is in the range from 6 to 60 wt %, more preferred in the range from 10 to 50 wt %, and particularly in the range from 15 to 40 wt %, based on the total amount of concentrated mother liquor.

At least a part of the concentrated mother liquor is recycled into the cooling step (III). To avoid an excessive accumulation of high boiling byproducts and contaminants it is preferred to recycle a part of the concentrated mother liquor into the cooling step (III) and to withdraw the rest of the concentrated mother liquor from the process. The amount of concentrated mother liquor recycled into the cooling step (III) preferably is in the range from 10 to 95 wt %, more preferred in the range from 40 to 90 wt %, and particularly in the range from 65 to 90 wt %, each based on the total amount of concentrated mother liquor.

The recycled concentrated mother liquor preferably is mixed with fresh organic phase and fed into the cooling (III). The ratio of fresh organic phase to concentrated mother liquor preferably is in the range from 60:1 to 6:1, more preferred in the range from 15:1 to 7:1 and particularly in the range from 10:1 to 7:1. The amount of concentrated mother liquor recycled into the cooling (III) preferably is set such that the amount of isomers of DCDPSO, particularly the amount of 2,4-dichlorodiphenyl sulfoxide, totally fed into the cooling (III) is in the range from 0 to 40 wt % and particularly in the range from 10 to 30 wt % based on the total amount of liquid fed into the cooling (III). The total amount of liquid fed into the cooling (III) is the sum of the organic phase containing DCDPSO obtained by mixing aqueous hydrochloric acid and intermediate product (II) and the recycled concentrated mother liquor. If the amount of isomers in the concentrated mother liquor rises, the part recycled into the cooling (III) is advantageously reduced, whereas a smaller amount of isomers in the concentrated mother liquor allows a larger part to be recycled as long as the amount of isomers in the organic phase obtained by mixing aqueous hydrochloric acid and intermediate product (II) remains constant.

Mixing of the recycled concentrated mother liquor and the fresh organic phase can be carried out before feeding into the apparatus in which the cooling and crystallization takes place such that a mixture of recycled concentrated mother liquor and fresh organic phase is fed into the apparatus. Alternatively, the recycled concentrated mother liquor and the fresh organic phase are fed separately into the apparatus in which the cooling and crystallization takes place and are mixed in this apparatus.

By concentrating and recycling at least a part of the mother liquor, the yield of DCDPSO can usually be increased considerably, such as up to about 10%, typically an increase of at least about 8 or 9%. This allows for carrying out the crystallization in only one step.

After solid-liquid-separation, the resulting moist DCDPSO preferably is washed with a washing liquid, particularly with solvent. By washing the moist DCDPSO with solvent, impurities which may attach to the surface of the crystallized DCDPSO can be removed. Using the solvent for washing the moist DCDPSO has the additional advantage that impurities adhering to the surface of the crystallized DCDPSO can be removed because the DCDPSO starts to solve at the surface and thus the impurities adhering to the surface loosen and can be removed.

If the solid-liquid-separation is a filtration, it is possible to carry out the following washing of the filter cake in the filtration apparatus, independently of whether the filtration is operated continuously or batchwise. After washing, the filter cake is removed as product.

In a continuous solid-liquid-separation process, the moist DCDPSO can be removed continuously from the solid-liquid-separation apparatus and afterwards the washing of the moist DCDPSO takes place. In the case the solid-liquid separation is a filtration and a continuous belt filter is used, it is preferred to filtrate the suspension, to transport the thus originating filter cake on the filter belt and to wash the filter cake at a different position in the same filtration apparatus.

If the solid-liquid separation is a filtration process, it is further also possible to operate the filtration semi-continuously. In this case the suspension is fed continuously into the filtration apparatus and the filtration is performed for a specified process time. Afterwards the filter cake produced during the filtration is washed in the same filtration apparatus. The process time for performing the filtration for example may depend on the differential pressure. Due to the increasing filter cake the differential pressure in the filtration apparatus increases. To determine the process time for the filtration, it is for example possible to define a target differential pressure up to which the filtration is carried out in a first filtration apparatus. Thereafter the suspension is fed into a second or further filtration apparatus in which filtration is continued. This allows for continuously performing the filtration. In those apparatus where the filtration is completed, the filter cake can be washed and withdrawn after finishing the washing. If necessary, the filtration apparatus can be cleaned after the filter cake is withdrawn. After the filter cake is withdrawn and the filter apparatus is cleaned when necessary, the filtration apparatus can be used again for filtration. If the washing of the filter cake and the optional cleaning of the filtration apparatus needs more time than the time for the filtration in one filtration apparatus, at least two filtration apparatus are used to allow continuous feeding of the suspension in a filtration apparatus while in the other apparatus the filter cake is washed or the filtration apparatus are cleaned.

In each filtration apparatus of the semi-continuous process, the filtration is carried out batchwise. Therefore, if the filtration and washing are carried out batchwise, the process corresponds to the process in one apparatus of the above described semi-continuous process.

To reduce the amount of solvent used in the process, preferably at least a part of the solvent is purified after being used for washing the moist DCDPSO and recycled. The purification of the solvent can be carried out by each process known by a person skilled in the art. Particularly suitable are distillation or evaporation processes to separate impurities from the solvent. In the inventive process, impurities which are washed out of the moist DCDPSO in the washing step particularly are remainders of by-products, isomers of the DCDPSO and auxiliaries like catalysts used for the production of the DCDPSO. As these impurities which are washed out of the moist DCDPSO usually are higher boiling than the solvent, the purification of the solvent can be carried out by evaporation in which the solvent is evaporated and condensed in a subsequent condenser. In a distillation process, the solvent is removed from the distillation apparatus, preferably a distillation column, as top stream and the bottom stream withdrawn from the distillation column contains the impurities. If the bottom stream still contains DCDPSO, it is also possible to recycle a part of the bottom stream into the cooling (III) to improve the yield and to reduce the amount of DCDPSO which is withdrawn from the process.

The thus purified solvent for example can be reused for washing the moist DCDPSO. Alternatively, it is also possible to recycle at least a part of the purified solvent into step (I).

It is preferred that the solvent used for washing the moist DCDPSO comprises less than 1 wt % impurities based on the total mass of the solvent. Therefore, if purified solvent is used for washing the moist DCDPSO, it is preferred to monitor the purity of the solvent after the purifying step. If the amount of impurities in the purified solvent exceeds 1 wt %, it is possible for example to add pure solvent in such an amount that the content of impurities in the mixed solvent is below 1 wt %. To achieve the necessary purity, it is also possible to add further purification steps, for example a second evaporation or distillation step.

It is also possible to use solvent which is less pure. The less pure solvent can for instance originate from a recycling process and can be used in a first washing. Thereafter—in one or more washing it is possible to employ more and more pure solvent.

Besides carrying out filtration and washing of the filter cake in one apparatus, it is also possible to withdraw the filter cake from the filtration apparatus and wash it in a subsequent washing apparatus. If the filtration is carried out in a belt filter, it is possible to convey the filter cake on the filter belt into the washing apparatus. For this purpose, the filter belt is designed in such a way that it leaves the filtration apparatus and enters into the washing apparatus. Besides transporting the filter cake on a filter belt from the filtration apparatus into the washing apparatus, it is also possible to collect the filter cake with a suitable conveyor and feed the filter cake from the conveyor into the washing apparatus. If the filter cake is withdrawn from the filtration apparatus with a suitable conveyor, the filter cake can be withdrawn from the filtration apparatus as a whole, or in smaller pieces such as chunks or pulverulent. Chunks for instance arise if the filter cake breaks when it is withdrawn from the filtration apparatus. To achieve a pulverulent form, the filter cake usually must be comminuted. Independently from the state of the filter cake, for washing the filter cake is brought into contact with washing liquid, preferably with solvent. For example, the filter cake can be put on a suitable tray in the washing apparatus and the washing liquid flows through the tray and the filter cake. Further it is also possible to break the filter cake into smaller chunks or particles and to mix the chunks or particles with the washing liquid. Subsequently the thus produced mixture of chunks or particles of the filter cake and the washing liquid is filtrated to remove the washing liquid. If the washing is carried out in a separate washing apparatus, the washing apparatus can be any suitable apparatus. Preferably the washing apparatus is a filter apparatus which allows to use a smaller amount of washing liquid and to separate the washing liquid from the solid DCDPSO in only one apparatus. However, it is also possible to use for example a stirred tank as washing apparatus. In this case it is necessary to separate the washing liquid from the washed DCDPSO in a following step, for example by filtration or centrifugation.

If the solid-liquid-separation is carried out by centrifugation, depending on the centrifuge it might be necessary to use a separate washing apparatus for washing the moist DCDPSO. However, usually a centrifuge can be used which comprises a separation zone and a washing zone or the washing can be carried out after centrifuging in the centrifuge.

Washing of the moist DCDPSO preferably is operated at ambient temperature. It is also possible to wash the moist DCDPSO at temperatures different to ambient temperature, for instance above ambient temperature. To avoid dissolving the DCDPSO in the solvent, it is preferred to keep the washing temperature at a temperature where the solubility of DCDPSO in the solvent is very low, preferably from 0 to 5 wt % based on the sum of DCDPSO and solvent. If the washing is carried out in the filtration apparatus, for washing the filter cake a differential pressure must be established. This is possible for example by feeding the solvent for washing the filter cake at a pressure above ambient pressure and withdraw the solvent after passing the filter cake at a pressure below the pressure at which the solvent is fed, for example at ambient pressure. Further it is also possible to feed the solvent for washing the filter cake at ambient pressure and withdraw the solvent after passing the filter cake at a pressure below ambient pressure.

Each process step described above can be carried out in only one apparatus or in more than one apparatus depending on the apparatus size and the amounts of compounds to be added. If more than one apparatus is used for a process step, the apparatus can be operated simultaneously or—particularly in a batchwise operated process—at different time. This allows for example to carry out a process step in one apparatus while at the same time another apparatus for the same process step is maintained, for example cleaned. Further, in that process steps where the contents of the apparatus remain for a certain time after all components are added, for example the reaction or the hydrolysis, it is possible after feeding all compounds in one apparatus to feed the components into a further apparatus while the process in the first apparatus still continues. However, it is also possible to add the components into all apparatus simultaneously and to carry out the process steps in the apparatus also simultaneously.

Due to the corrosivity of the components used in the process, it is preferred to provide all surfaces which come into contact with the components, particularly surfaces of the at least one reactor in which the reaction and the hydrolysis are carried out, the surfaces of the cooling vessel and the washing apparatus for washing the organic phase, with an enamel layer. Pipes connecting the apparatus preferably are made of stainless steel with an enamel layer. The apparatus for solid-liquid separation, particularly the filtration apparatus, preferably is made of a nickel-base alloy or stainless steel with a corrosion resistant layer. If the solid-liquid-separation is a filtration, the filtration apparatus preferably comprises a filter element which is made of a material which has a good or very good chemical resistance. Such materials can be polymeric materials or chemical resistant metals as described above for the used apparatus. Filter elements for example can be filter cartridges, filter membranes, or filter cloth. If the filter element is a filter cloth, preferred materials additionally are flexible, particularly flexible polymeric materials such as those which can be fabricated into wovens. These can for instance be polymers which can be drawn or spun into fibers. Particularly preferred as material for the filter element are polyether ether ketone (PEEK), polyamide (PA) or fluorinated polyalkylenes, for example ethylene chlorotrifluoroethylene (ECTFE), polytetrafluoroethylene (PTFE), polyvinylidene fluoride (PVDF), fluorinated ethylene-propylene (FEP).

A BRIEF DESCRIPTION OF THE FIGURE

An illustrative embodiment of the invention is shown in the FIGURE and explained in more detail in the following description.

In the drawing:

FIG. 1 shows a schematic flow diagram of the process for producing DCDPSO,

The only FIGURE shows a schematic flow diagram of the process for producing DCDPSO in a first embodiment.

The process for producing DCDPSO according to the embodiment as shown in FIG. 1 is carried out in a first reaction 1 and a second reaction 3. Chlorobenzene 5, thionyl chloride 7 as reactants and aluminum chloride 9 as catalyst are fed into the first reaction 1. The reactants and the catalyst can be fed simultaneously into the first reaction 1. However, preferably aluminum chloride 9 and chlorobenzene 5 are firstly fed into the first reaction 1 and mixed and the thionyl chloride 7 is then added to the mixture of aluminum chloride and chlorobenzene in a controlled way. In the first reaction 1 an intermediate reaction product is produced which is solved in excess chlorobenzene. The first reaction 1 is carried out at a temperature in the range from 0 to below 20° C. and ambient pressure. After the reaction is completed, the intermediate reaction product is withdrawn from the first reaction 1 and fed into the second reaction 3. Additionally, aqueous hydrochloric acid 11 with a concentration in the range from 3 to 12 wt % is fed to the second reaction 3. In the second reaction 3 DCDPSO is produced from the intermediate product by hydrolysis.

The hydrolysis in the second reaction 3 is performed at a temperature in the range from 70 to 110° C. and at ambient pressure. After finishing the hydrolysis, a phase separation into an aqueous phase and an organic phase takes place. The aqueous phase 13 containing aluminum chloride is removed from the process and the organic phase 15 comprising DCDPSO as product and chlorobenzene is fed into a washing step 17.

In the washing step 17, the organic phase 15 comprising DCDPSO as product and chlorobenzene as solvent is mixed with water 18 to remove residual catalyst. The washing is performed at a temperature from 70 to 110° C. and at ambient pressure. After the washing, the mixture separates into two phases, an aqueous phase 21 comprising traces of chlorobenzene and aluminum chloride and an organic phase 19 comprising DCDPSO as product and chlorobenzene as solvent.

Besides the intermediate reaction product hydrogen chloride accrues during the first reaction 1. As the hydrogen chloride is gaseous, it easily can be withdrawn from the first reaction 1. The gaseous hydrogen chloride 23 preferably is fed into an absorbing step 25 as shown in the FIGURE. In the absorbing step 25 aqueous hydrochloric acid is produced by absorbing the hydrogen chloride in water. This aqueous hydrochloric acid preferably is used for the hydrolysis in the second reaction 3 as shown in the FIGURE.

The water for producing the aqueous hydrochloric acid in the absorption step 25 preferably is the aqueous phase 21 which emanates from the washing in the washing step 17. By using the aqueous phase 21 from the washing the total amount of fresh water can be reduced and thus a much smaller amount of wastewater accrues.

This wastewater is the aqueous phase 13 obtained in the hydrolysis in the second reaction 3. The wastewater can be disposed after cleaning.

After washing, the organic phase 19 comprising DCDPSO and solvent is fed into a crystallization step 27. In the crystallization step 27 the organic phase is cooled to a temperature below the saturation point of DCDPSO in the solvent. This has the effect that DCDPSO starts to crystallize and a suspension is formed comprising solid DCDPSO crystals in a liquid which contains solvent, DCDPSO which is not crystallized and liquid byproducts. This suspension is fed into a solid-liquid-separation step 29. By solid-liquid-separation the solid DCDPSO crystals are separated from the liquid phase obtaining solid DCDPSO 31 as product and mother liquor 33.

The solid-liquid-separation step 29 can be carried out in any suitable solid-liquid-separation apparatus, particularly in a filtration apparatus, for example an agitated pressure nutsche, a rotary pressure filter, a drum filter, a belt filter or a centrifuge. The differential pressure in the filtration apparatus preferably is in the range from 100 to 6000 mbar, more preferred in the range from 300 to 2000 mbar and particularly in the range from 400 to 1500 mbar. The filtration preferably is carried out at ambient temperature. Due to the necessary differential pressure in the filtration step, ambient pressure either can be set on the feed side which means that the pressure on the filtrate side is below ambient pressure, or ambient pressure is set on the filtrate side and a pressure above ambient pressure is set on the feed side.

The solid DCDPSO 31 is removed from the process and the mother liquor 33 is fed into a concentrating step 35. In the concentrating step 35, solvent 37 is removed from the mother liquor and preferably recycled into the first reaction 1 as shown in the FIGURE.

To remove by-products and impurities from the process which are not removed with the solvent, a part of the concentrated mother liquor is withdrawn as stream 39. The rest 41 of the concentrated mother liquor is recycled into the crystallization step 27.

The concentrating step 35 for example is a distillation or evaporation. In the distillation or evaporation solvent as low boiler is removed in gaseous form and the concentrated mother liquor containing the high boilers is removed in liquid form. If the mother liquor is concentrated by evaporation or distillation, the distillation or evaporation preferably is carried out at a pressure in the range from 20 to 800 mbar(abs), more preferred in a range from 50 to 500 mbar(abs), and particularly in a range from 100 to 350 mbar(abs). The bottom temperature if the concentrating step is operated by distillation or the temperature for evaporation preferably is in the range from 40 to 110° C., more preferred in the range from 55 to 100° C. and in particularly in the range from 55 to 80° C.

In the solid-liquid-separation step 29 a filter cake 43 is formed. In the embodiment shown in the FIGURE, the solid-liquid-separation is carried out by filtration and the filter cake 43 is washed in the filtration apparatus. For washing the filter cake 43, solvent 45 is fed into the filtration apparatus at a position at which the filtration is finished. After washing, the filter cake 43 is removed from the filtration apparatus as solid DCDPSO 31 as product.

If the filtration and washing are carried out continuously in one apparatus, the filtration apparatus preferably is a belt filter. In the belt filter the suspension is fed on one end of a filter belt and transported through the filtration apparatus. While being transported through the filtration apparatus the suspension is filtered forming the filter cake 43 and the mother liquor 33. After a certain filtration duration which depends on the length and the speed of the filter belt, the solvent 45 for washing the filter cake 43 is added. For washing the filter cake 43, the solvent passes the filter cake and the filter belt on which the filter cake 43 lies and is collected below the filter belt and withdrawn from the filtration apparatus.

Besides using one apparatus for filtration and washing as shown in the FIGURE, it is also possible to use one solid-liquid-separation apparatus in which the suspension is filtered forming a filter cake and mother liquor and a second apparatus into which the filter cake is transferred and then washed. Further, if the filtration and washing are carried out batchwise, first the suspension is filtered and the filter cake obtained by the filtration is washed in the same apparatus. In the batchwise process, however, unlike a continuous process, it is not necessary to transport the filter cake. Therefore, also filter apparatus can be used which do not convey the filter cake, for example an agitated pressure nutsche. Besides a filter apparatus for batchwise filtration, alternatively a batch centrifuge can be used for the solid-liquid separation.

The mother liquor 33 and the solvent used for washing 47 are withdrawn from the filtration apparatus and fed into the concentrating step 35. By feeding the solvent used for washing 47 feeding into the concentrating step 35, DCDPSO which can be removed by washing can be recovered. Further, in the concentrating step 35 impurities can be removed from the solvent to obtain a purified solvent. Besides recycling the solvent 37 into the first reaction 1, at least a part of the thus purified solvent also can be reused for washing the filter cake.

Besides adding the mother liquor obtained in the solid-liquid-separation and the solvent from the washing step to one purifying step as shown in the FIGURE, it is also possible to concentrate the mother liquor and to purify the solvent from the washing step separately. In this case concentrating the mother liquor and purifying the solvent preferably both are carried out by distillation or evaporation, wherein the solvent in both distillations and/or evaporations is the low boiler and is withdrawn in gaseous form and the concentrated mother liquor and the impurities from the washing process are the high boiler and in liquid form, respectively. The concentrated mother liquor can be used in the step for producing the suspension and the high boilers which are obtained by distillation or evaporation in the purifying step of the solvent used for washing are removed.

Further, it is also possible to carry out the concentration of the mother liquor and the purification separately but to further purify the solvent removed from the mother liquor in the concentrating process add the solvent removed from the mother liquor into the process for purifying the solvent, too.

EXAMPLES

Example 1

5.5 mol aluminum chloride and 40 mol chlorobenzene were fed into a stirred tank reactor as first reactor. 5 mol thionyl chloride were added to the reaction mixture in 160 min. The reaction in the first reactor was carried out at 10° C. Hydrogen chloride produced in the reaction was withdrawn from the process. After finishing the addition of thionyl chloride the reaction mixture was heated to 60° C.

After finishing the reaction in the first reactor the resulting reaction mixture was fed into a second stirred tank reactor which contained 3400 g hydrochloric acid with a concentration of 11 wt %. The second stirred tank reactor was heated to a temperature of 90° C. After 30 min the mixing was stopped and the mixture separated into an aqueous phase and an organic phase.

The aqueous phase was withdrawn and the organic phase was washed with 3000 g water while stirring at 90° C. After washing, stirring was stopped and the mixture separated into an aqueous phase and an organic phase.

The aqueous phase was removed and the organic phase was subjected to a distillation. Monochlorobenzene was distilled from the organic phase until saturation was reached at about 88° C. (monitored via a turbidity probe, distillation conditions: 200 mbar(abs)). Then the organic phase was cooled by reducing the pressure until the temperature reached 30° C.

By the cooling a suspension was obtained containing crystallized DCDPSO. The suspension then was filtrated to obtain a filter cake comprising the crystallized DCDPSO.

After filtration and washing of the filter cake with monochlorobenzene the crystallized DCDPSO was dried at 100° C. and 100 mbar(abs).

The DCDPSO in the liquid phase was cooled by reducing the pressure was obtained in 83.2% yield, with a purity of 98.8 wt %, containing 0.6 wt % monochlorobenzene, 0.2 wt % 4,4'-dichlorodiphenylsulfide and 0.4 wt % 2,4'-dichlorodiphenylsulfoxide.

Example 2

5.5 mol aluminum chloride and 40 mol chlorobenzene were fed into a stirred tank reactor as first reactor. 5 mol thionyl chloride were added to the reaction mixture in 160 min. The reaction in the first reactor was carried out at 10° C. Hydrogen chloride produced in the reaction was withdrawn from the process. After finishing the addition of thionyl chloride the reaction mixture was heated to 60° C.

After finishing the reaction in the first reactor, the resulting reaction mixture was fed into a second stirred tank reactor which contained 3400 g hydrochloric acid with a concentration of 11 wt %. The second stirred tank reactor was heated to a temperature of 90° C. After 30 min the mixing was stopped and the mixture separated into an aqueous phase and an organic phase. The aqueous phase was withdrawn and the organic phase was washed with 3000 g water while stirring at 90° C. After washing, stirring was stopped and the mixture separated into an aqueous phase and an organic phase.

The aqueous phase was removed and the organic phase was subjected to a distillation. Monochlorobenzene was distilled from the organic phase until saturation was reached at about 88° C. (monitored via a turbidity probe, distillation conditions: 200 mbar(abs)). The organic phase was cooled by reducing the pressure until the temperature reached 30° C.

By the cooling a suspension was obtained containing crystallized DCDPSO. The suspension then was filtrated to obtain a filter cake comprising crystallized DCDPSO.

After filtration and washing of the filter cake with monochlorobenzene the crystalline solid was dried at 100° C. and 100 mbar(abs). The combined mother liquor and the monochlorobenzene which was used for washing were subjected to a distillation. In the distillation monochlorobenzene was removed until the amount of combined mother liquor and washing filtrate was reduced to 25 wt %. The distillation was operated at a bottom temperature of 90° C. and 200 mbar (abs).

While the distilled monochlorobenzene was reused in the next batch as starting material, 80 wt % of the obtained bottom product were transferred into the crystallization of the next batch.

The 4,4'-dichlorodiphenyl sulfoxide yield in the steady state was 1232 g, which corresponds to 91.3%.

The 4,4'-dichlorodiphenyl sulfoxide had a purity of 98.9 wt %, containing 0.5 wt % monochlorobenzene, 0.3 wt % 4,4'-dichlorodiphenylsulfide and 0.3 wt % 2,4'-dichlorodiphenylsulfoxide.

LIST OF REFERENCE NUMERALS 1 first reaction
3 second reaction
5 chlorobenzene
7 thionyl chloride
9 aluminum chloride
11 aqueous hydrochloric acid
13 aqueous phase
15 organic phase
17 washing step
18 water
19 organic phase
21 aqueous phase
23 gaseous hydrogen chloride
25 absorbing step
27 crystallization step
29 solid-liquid-separation step
31 solid DCDPSO
33 mother liquor
35 concentrating step
37 solvent
39 concentrated mother liquor
41 concentrated mother liquor
43 filter cake
45 solvent
47 solvent used for washing

The invention claimed is:

1. A process for producing 4,4'-dichlorodiphenyl sulfoxide comprising:
(I) reacting thionyl chloride, chlorobenzene and aluminum chloride in a molar ratio of thionyl chloride: chlorobenzene:aluminum chloride of 1:(6 to 9):(1 to 1.5) at a temperature in the range from 0 to below 20° C., forming an intermediate reaction product and hydrogen chloride;
(II) mixing aqueous hydrochloric acid and the intermediate reaction product at a temperature in the range from 70 to 110° C. to obtain an organic phase comprising 4,4'-dichlorodiphenyl sulfoxide and an aqueous phase;
(III) cooling the organic phase comprising the 4,4'-dichlorodiphenyl sulfoxide to a temperature below the saturation point of 4,4'-dichlorodiphenyl sulfoxide to obtain a suspension comprising crystallized 4,4'-dichlorodiphenyl sulfoxide, wherein cooling of the organic phase is carried out in a gastight closed vessel by
(i) reducing the pressure in the gastight closed vessel;
(ii) evaporating chlorobenzene;
(iii) condensing the evaporated chlorobenzene by cooling;
(iv) returning the condensed chlorobenzene into the gastight closed vessel;
(IV) solid-liquid-separation of the suspension to obtain a residual moisture containing solid 4,4'-dichlorodiphenyl sulfoxide comprising crystallized 4,4'-dichlorodiphenyl sulfoxide and mother liquor.

2. The process according to claim 1, wherein the organic phase obtained in (II) is separated off and washed with water at a temperature in the range from 70 to 110° C. before cooling in (III).

3. The process according to claim 1, wherein the hydrogen chloride obtained in (I) is mixed with water to obtain the aqueous hydrochloric acid which is used in (II).

4. The process according to claim 2, wherein the water which is used for washing the organic phase is separated off and mixed with the hydrogen chloride obtained in (I) to obtain the aqueous hydrochloric acid.

5. The process according to claim 1, wherein in (I) aluminum chloride and chlorobenzene are first fed into a reactor and the thionyl chloride is added to the aluminum chloride and chlorobenzene.

6. The process according to claim 1, wherein for initializing crystallization of the 4,4'-dichlorodiphenyl sulfoxide the following steps are carried out before setting the reduced pressure in step (i):
reducing the pressure in the vessel such that the boiling point of the organic phase is in the range from 80 to 95° C.;
evaporating chlorobenzene until an initial formation of solids takes place;
increasing the pressure in the vessel and heating the organic phase in the vessel to a temperature in the range from 85 to 100° C.

7. The process according to claim 1, wherein the mother liquor obtained in (IV) is concentrated and at least a part of the concentrated mother liquor is recycled into the cooling of the organic phase.

8. The process according to claim 7, wherein the mother liquor is concentrated by distillation or evaporation.

9. The process according to claim 7, wherein the amount of concentrated mother liquor recycled into the cooling of the organic phase is in the range from 10 to 95 wt % based on the total amount of concentrated mother liquor.

10. The process according to claim 1, wherein the residual moisture containing solid 4,4'-dichlorodiphenyl sulfoxide obtained in (IV) is washed with solvent.

11. The process according to claim 10, wherein at least a part of the solvent is purified after being used for washing the residual moisture containing solid 4,4'-dichlorodiphenyl sulfoxide and recycled.

12. The process according to claim 11, wherein at least a part of the purified solvent is recycled into step (I).

13. The process according to claim 12, wherein at least a part of the purified solvent is reused for washing the residual moisture containing solid 4,4'-dichlorodiphenyl sulfoxide.

* * * * *